(12) United States Patent
Dobeck et al.

(10) Patent No.: US 9,291,530 B1
(45) Date of Patent: Mar. 22, 2016

(54) APPARATUS AND METHOD FOR SAMPLING AND ANALYZING EXHAUST GAS OR LIQUID

(71) Applicants: Mark E. Dobeck, Bozeman, MT (US); Jacob Fraser, Bozeman, MT (US)

(72) Inventors: Mark E. Dobeck, Bozeman, MT (US); Jacob Fraser, Bozeman, MT (US)

(73) Assignee: Techlusion Corporation, Belgrade, MT (US)

( * ) Notice: Subject to any disclaimer, the term of this patent is extended or adjusted under 35 U.S.C. 154(b) by 378 days.

(21) Appl. No.: 13/916,674

(22) Filed: Jun. 13, 2013

Related U.S. Application Data

(60) Provisional application No. 61/659,123, filed on Jun. 13, 2012.

(51) Int. Cl.
*G01N 1/22* (2006.01)
*G01N 1/20* (2006.01)
*G01N 33/00* (2006.01)

(52) U.S. Cl.
CPC .......... *G01N 1/2035* (2013.01); *G01N 33/0011* (2013.01)

(58) Field of Classification Search
CPC .............. G01N 1/2252; G01N 1/2035; G01N 2001/205; G01N 2001/2057; G01N 2001/2267
USPC ........................................................ 73/23.31
See application file for complete search history.

(56) References Cited

U.S. PATENT DOCUMENTS

| | | | | |
|---|---|---|---|---|
| 3,890,100 A * | 6/1975 | Busch | ................ | G01N 33/0011 376/256 |
| 4,253,336 A * | 3/1981 | Pietzuch | .............. | G01N 1/2273 73/864.74 |
| 4,373,377 A * | 2/1983 | Smith | ...................... | F16J 15/46 285/97 |
| 4,974,455 A * | 12/1990 | McGowan | .......... | G01N 1/2258 73/863.12 |
| 5,239,877 A * | 8/1993 | Suddath | .................... | B01L 5/02 137/561 A |
| 5,410,907 A * | 5/1995 | Strom | .................... | F02M 17/04 73/23.31 |
| 6,289,752 B1 * | 9/2001 | Nimberger | ........... | G01N 1/2035 73/863.11 |
| 6,360,619 B1 * | 3/2002 | Schultz, Jr. | ............... | F17D 3/10 137/613 |
| 6,764,536 B2 * | 7/2004 | Welker | ................. | G01N 1/2247 55/417 |
| 8,256,307 B2 * | 9/2012 | Graze, Jr. | ............. | G01N 1/2252 73/23.31 |
| 2010/0101302 A1 * | 4/2010 | Graze, Jr. | ............. | G01N 1/2252 73/23.31 |

* cited by examiner

*Primary Examiner* — Freddie Kirkland, III
(74) *Attorney, Agent, or Firm* — MacMillan, Sobanski & Todd, LLC

(57) ABSTRACT

An apparatus and method are disclosed for sampling and analyzing the exhaust gas or liquid from an internal combustion engine or other device that generates a flow of exhaust gas or liquid during use. The apparatus includes a connector that is adapted to be secured adjacent to an aperture formed through an outlet conduit of an engine or other device that generates a flow of exhaust gas or liquid therethrough during use. A conduit communicates with the connector and is adapted to receive and pass therethrough at least a portion of the exhaust gas or liquid from the outlet conduit. A sensor chamber communicates with the conduit and is adapted to receive and pass therethrough at least a portion of the exhaust gas or liquid from the conduit. A one-way valve only allows the exhaust gas or liquid in the sensor chamber to exit therefrom. Lastly, a sensor senses at least one characteristic of the exhaust gas or liquid in the sensor chamber and generates a signal that is representative of such characteristic.

15 Claims, 2 Drawing Sheets

US 9,291,530 B1

APPARATUS AND METHOD FOR SAMPLING AND ANALYZING EXHAUST GAS OR LIQUID

CROSS-REFERENCE TO RELATED APPLICATIONS

This application claims the benefit of U.S. Provisional Application No. 61/659,123 filed Jun. 13, 2012, the disclosure of which is incorporated herein by reference.

BACKGROUND OF THE INVENTION

This invention relates in general to internal combustion engines and other devices that generate a flow of exhaust gas or liquid during use. More specifically, this invention relates to a simple and accurate apparatus and method for sampling and analyzing such exhaust gas or liquid.

Sensors are commonly used in the exhaust systems of internal combustion engines and other devices that generate a flow of exhaust gas or liquid during use in order to measure a variety of parameters, such as an air-to-fuel ratio of the exhaust gas. One common method of sensor installation is to drill a hole in a portion of the exhaust system, then weld a nut (sometimes referred to as a bung) over the hole such that a sensor can be screwed through the nut and the hole into the portion of the exhaust system to measure the desired parameter. In another common method, the sensor is attached to a tube that, in turn, is inserted into a tailpipe or other output component of the exhaust system to measure the desired parameter.

Although the known methods have been effective, several disadvantages have been noted. The welded bung method permits the sensor to make relatively accurate measurements, but involves the use of specialized tools and a knowledgeable installer. Therefore, the welded bung method is relatively complicated and expensive to perform. The tailpipe insertion method, on the other hand, is much simpler and inexpensive to perform, but can be less accurate because of the potential for exhaust gas reversion, which can cause the sensor to be exposed to a mixture of the exhaust gas with ambient air from outside the tailpipe. This can occur because many tailpipes have baffles or bends that can make it difficult to insert a tube sufficiently far within the tailpipe to avoid the effects of reversion. Thus, it would be desirable to provide a simple and accurate apparatus and method for sampling and analyzing the exhaust gas or liquid generated from an internal combustion engine or other device that avoids these problems.

SUMMARY OF THE INVENTION

This invention relates to an apparatus and method are disclosed for sampling and analyzing the exhaust gas or liquid from an internal combustion engine or other device that generates a flow of exhaust gas or liquid during use. The apparatus includes a connector that is adapted to be secured adjacent to an aperture formed through an outlet conduit of an engine or other device that generates a flow of exhaust gas or liquid therethrough during use. A conduit communicates with the connector and is adapted to receive and pass therethrough at least a portion of the exhaust gas or liquid from the outlet conduit. A sensor chamber communicates with the conduit and is adapted to receive and pass therethrough at least a portion of the exhaust gas or liquid from the conduit. A one-way valve only allows the exhaust gas or liquid in the sensor chamber to exit therefrom. Lastly, a sensor senses at least one characteristic of the exhaust gas or liquid in the sensor chamber and generates a signal that is representative of such characteristic.

Various objects and advantages of this invention will become apparent to those skilled in the art from the following detailed description of the preferred embodiment, when read in light of the accompanying drawings.

DETAILED DESCRIPTION OF THE PREFERRED EMBODIMENT

Figure 1:
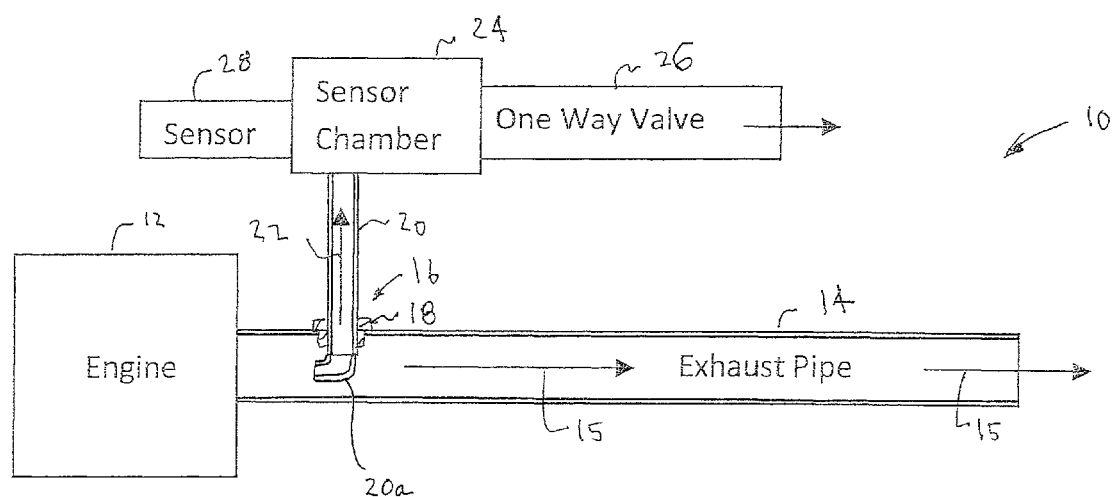
FIG. 1 is a block diagram of an improved apparatus to analyze the exhaust gas and/or liquid flow generated from an internal combustion engine or other device in accordance with this invention.

Referring now to the drawings, there is illustrated in FIG. 1 an exhaust gas sampling apparatus, indicated generally at 10, in accordance with this invention. As shown therein, the apparatus 10 may be used in combination with a conventional engine 12. For example, the engine 12 may be an internal combustion engine 12 in which combustion is intermittent, such as a well known two-stroke or four-stroke piston engine and its variants, such as a six-stroke piston engine and a Wankel rotary engine. However, it will be appreciated that this invention can be used with any device that generates a flow of exhaust gas or liquid during use. The engine 12 vents exhaust gas through an outlet conduit, such as an exhaust pipe 14. In FIG. 1, arrows 15 shown within the exhaust pipe 14 illustrate the direction of the flow of the exhaust gas through the exhaust pipe 14.

An aperture, indicated generally at 16, is formed through the exhaust pipe 14. The aperture 16 can be formed by any desired method, such as by conventionally drilling a hole through a wall of the exhaust pipe, and is preferably relatively small in size. The aperture 16 is preferably drilled through the exhaust pipe 14 at a location that is relatively close to the engine 12 and relatively remote from the end of the exhaust pipe 14. After the aperture 16 has been formed through the exhaust pipe 14, a connector, such as a conventional rivet nut 18, is secured to the exhaust pipe 14 adjacent to the aperture 16. The rivet nut 18 (also known as a blind nut) can be embodied as a one-piece, internally-threaded, and counterbored tubular rivet that can be anchored to the exhaust pipe 14 entirely from one side (i.e., the outside thereof). The rivet nut 18 may be installed on the exhaust pipe 14 in any desired manner. For example, the rivet nut 18 may be designed to form a bulge during installation on the inside wall of the exhaust pipe as an installation screw (not shown) or similar tool is tightened in its threads. Alternatively, the rivet nut 18 may be designed to be similarly deformed using a screw, but drawn into the exhaust pipe instead of creating a bulge.

Regardless of the specific installation process, after the rivet nut 18 has been installed on the exhaust pipe 14, a first end of a conduit 20 can be secured to the rivet nut 18 as shown in FIG. 1. The conduit 20 is conventional in the art and may, for example, be embodied as any hollow tube or similar structure that can receive and pass therethrough at least a portion of the exhaust gas from the exhaust pipe 14, as indicated by an arrow 22 in FIG. 1. Thus, the conduit 20 communicates with the rivet nut 18 and is adapted to receive and pass therethrough at least a portion of the exhaust gas or liquid from the exhaust pipe 14. The conduit 20 may be rigid or flexible as desired, and may further be formed from any desired material, such as metal, plastic, and the like. For example, the conduit 20 may be formed from a rigid metallic material, which would allow the first end of the conduit 20 to be externally threaded so as to cooperate with the internally threaded portion of the rivet nut 18.

If desired, an optional intake scoop 20a may be provided on the first end of the conduit 20 that is disposed within the exhaust pipe 14. The intake scoop 20a may be embodied as any desired structure and is provided to help direct a portion of the exhaust gas passing through the exhaust pipe 14 (in the direction of the arrows 15) into the conduit 20 (in the direction of the arrow 22).

With or without the intake scoop 20a, when the first end of the conduit 20 is secured to the rivet nut 18, a portion of the exhaust gas from the engine 12 flows out of the exhaust pipe 14 and through the conduit 20 (as indicated by the arrow 22 in FIG. 1) into a sensor chamber 24 that is provided at a second end of the conduit 20. Thus, the sensor chamber 24 communicates with the conduit 20 and is adapted to receive and pass therethrough at least a portion of the exhaust gas or liquid from the conduit 20.

That portion of the exhaust gas then exits the sensor chamber 24 through a one-way valve 26 to the atmosphere. The one-way valve 26 is conventional in the art and is provided to ensure that reversion does not occur within the sensor chamber 24. Thus, the one-way valve 26 only allows the exhaust gas or liquid in the sensor chamber 24 to exit therefrom. The one-way valve 26 may, for example, be embodied as a conventional reed valve. Alternatively, the one-way valve 26 may be embodied as a conventional bubble chamber apparatus, including a chamber containing a liquid (such as water, for example) and a tube having an end that extends into the liquid in the chamber. This arrangement allows the exhaust gas from the conduit 22 to bubble through the liquid and exit the sensor chamber 24, but prevents any gas from flowing in the opposite direction into the sensor chamber 24. Additionally, such a bubble chamber apparatus could additionally function as a visual indicator that the engine 12 is operating, inasmuch as bubbles would be created in the liquid when the exhaust gas is flowing through the bubble chamber apparatus.

A sensor 28 is provided for sensing at least one characteristic of the exhaust gas or liquid in the sensor chamber 24 and for generating a signal that is representative of such characteristic. The sensor 28 is conventional in the art and may be embodied as any desired device or combination of devices for sensing any desired characteristic or combination of characteristics of the exhaust gas or liquid in the sensor chamber 24. For example, the sensor 28 may be a conventional oxygen sensor that is frequently used to facilitate the operation of an electronic fuel injection and emission control system. To accomplish this, the sensor 28 may be disposed within the sensor chamber 24 and connected to a conventional electronic controller (not shown) for the engine 12 and, therefore, provide the sensed exhaust gas data for optimal control of the engine 12. As is well known, such engine controllers analyze the sensed exhaust gas data provided by the sensor 28 and may utilize closed-loop, feedback-controlled fuel injection techniques to vary the fuel injector output according to real-time data from the sensor 28, rather than operating with a predetermined, open-loop fuel map. In addition to enabling electronic fuel injection to work efficiently, such an emissions control technique can reduce the amounts of both unburned fuel and oxides of nitrogen entering the atmosphere.

Following installation, the apparatus 10 of this invention may, if desired, be left in place as a permanent installation the exhaust pipe 14. Alternatively, the apparatus 10 may be removed at any time from the exhaust pipe 14 because the aperture 16 can be easily plugged after the removal of the conduit 20. The apparatus 10 has the advantages of the previously described prior art systems and none of the disadvantages. The system 10 is easy to install with common tools, supplies uncontaminated gas to the sensor, and can be easily removed.

It will be appreciated that the apparatus 10 of this invention may be applied outside of the illustrated use for sampling exhaust gas from an internal combustion engine. This could include, for example, measuring any type of gas or liquid sampling or sampling of exhaust from non-internal combustion engines. Thus, although the invention has been described as including an oxygen sensor, it will be appreciated that the invention also may be practiced with other types of gas or material sensors.

Figure 2:
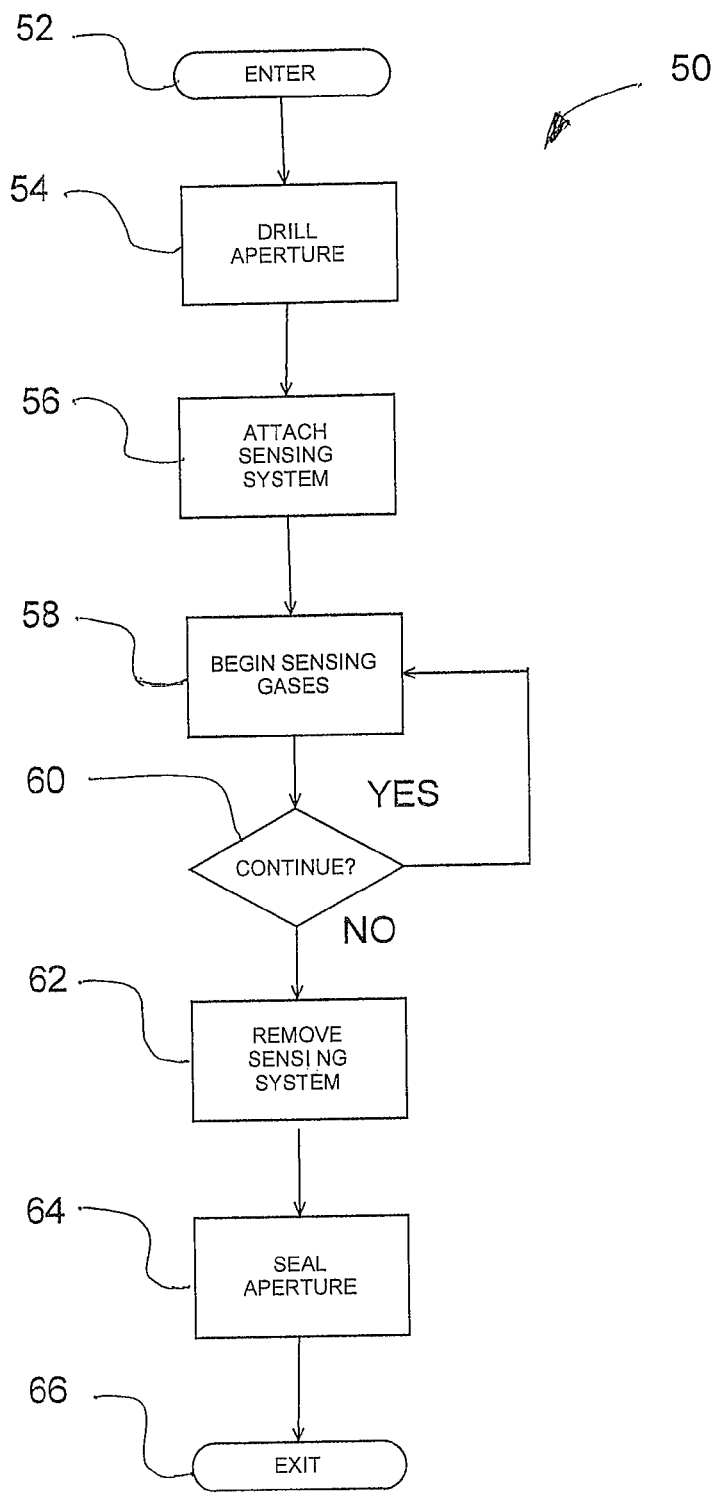
FIG. 2 is a flowchart of an improved method to analyze the exhaust gas and/or liquid flow from an internal combustion engine or other device using the apparatus illustrated in FIG. 1.

This invention also contemplates a method for sampling and analyzing exhaust gas, such as illustrated by a flow chart 50 shown in FIG. 2. The method 50 is entered through block 52 and proceeds to functional block 54, where the aperture 16 is drilled or otherwise formed through the exhaust pipe 14. The method 50 then continues to functional block 56, where the sensing apparatus 10 described above is attached to the exhaust pipe 14. As described above, the sensing apparatus 10 communicates with the exhaust gas from the engine 12 via the aperture 16. Once installed, the sampling apparatus 10 is activated and begins sampling and analyzing the exhaust gas in functional block 58 of the method 50.

Periodically, the method advances to decision block 60, where predetermined criteria are checked for continuation of the sampling. If, in decision block 60, the criteria for continued sampling are met, the method 50 transfers back to functional block 58 and continues sampling the exhaust gas. If, however, in decision block 60, the criteria for continued sampling are not met, the method 50 transfers to functional block 62, wherein the sampling apparatus 10 is removed. The method 50 then continues to functional block 64, where the aperture 16 drilled through the exhaust pipe 14 is sealed. Thereafter, the method 50 exits through block 66.

It will be appreciated that the flowchart shown in FIG. 2 is intended to be exemplary and that, therefore, the invention may also be practiced with a sequence of actions that differs from that shown in FIG. 2.

In accordance with the provisions of the patent statutes, the principle and mode of operation of this invention have been explained and illustrated in its preferred embodiment. However, it must be understood that this invention may be practiced otherwise than as specifically explained and illustrated without departing from its spirit or scope.

What is claimed is:

1. An apparatus for sampling and analyzing an exhaust gas or liquid generated from an engine or device having an outlet conduit, the apparatus comprising:

a connector that is adapted to be secured adjacent to an aperture formed through an outlet conduit of an engine or device that generates a flow of exhaust gas or liquid therethrough during use;

a conduit having a first end and a second end, the first end attached to the connector, the conduit adapted to receive and pass therethrough at least a portion of the exhaust gas or liquid from the outlet conduit;

a sensor chamber attached to the second end of the conduit, the sensor chamber in fluid communication with the conduit and is adapted to receive and pass therethrough at least a portion of the exhaust gas or liquid from the conduit;

a one-way valve attached to the sensor chamber and defining a flow path between the sensor chamber and the environment outside of the apparatus, the one-way valve only allowing the exhaust gas or liquid in the sensor chamber to exit therefrom; and a sensor, a portion of which is disposed in the sensor chamber and upstream of the one-way valve, the sensor sensing at least one characteristic of the exhaust gas or liquid in the sensor chamber and generating a signal that is representative of such characteristic.

2. The apparatus defined in claim 1 wherein the connector is a rivet nut.

3. The apparatus defined in claim 1 wherein the conduit is secured to the connector.

4. The apparatus defined in claim 3 wherein the conduit is externally threaded and cooperates with an internally threaded portion of the connector.

5. The apparatus defined in claim 1 wherein the conduit includes an intake scoop that is adapted to be disposed within the outlet conduit of an engine or other device that generates a flow of exhaust gas or liquid therethrough during use.

6. The apparatus defined in claim 1 wherein the one-way valve is a reed valve.

7. The apparatus defined in claim 1 wherein the one-way valve is a bubble chamber apparatus.

8. A method for sampling and analyzing an exhaust gas or liquid generated from an engine or device having an outlet conduit, the method comprising the steps of:

(a) securing a connector adjacent to an aperture formed through an outlet conduit of an engine or device that generates a flow of exhaust gas or liquid therethrough during use;

(b) conducting at least a portion of the exhaust gas or liquid from the outlet conduit to a sensor chamber;

(c) conducting the exhaust gas or liquid in the sensor chamber through a one-way valve that only allows the exhaust gas or liquid in the sensor chamber to exit therefrom; and (d) sensing at least one characteristic of the exhaust gas or liquid in the sensor chamber at a location upstream of the one-way valve, and generating a signal that is representative of such characteristic.

9. The method defined in claim 8 wherein step (a) is performed by securing a rivet nut adjacent to the aperture.

10. The method defined in claim 8 wherein step (b) is performed by securing a first end of the conduit to the connector and securing a second end of the conduit to the sensor chamber.

11. The method defined in claim 10 wherein the conduit is externally threaded and cooperates with an internally threaded portion of the connector.

12. The method defined in claim 10 wherein the connector includes an intake scoop that is adapted to be disposed within the outlet conduit of an engine or other device that generates a flow of exhaust gas or liquid therethrough during use.

13. The method defined in claim 8 wherein step (c) is performed by conducting the exhaust gas or liquid in the sensor chamber through a reed valve.

14. The method defined in claim 8 wherein step (c) is performed by conducting the exhaust gas or liquid in the sensor chamber through a bubble chamber apparatus.

15. The method defined in claim 8 wherein step (d) is performed by disposing a sensor within the sensor chamber.

* * * * *